US008877931B2

(12) United States Patent
Pcion et al.

(10) Patent No.: US 8,877,931 B2
(45) Date of Patent: Nov. 4, 2014

(54) PROCESS AND INTERMEDIATES FOR PREPARING INTEGRASE INHIBITORS

(71) Applicant: Gilead Sciences, Inc., Foster City, CA (US)

(72) Inventors: Dominika Pcion, San Francisco, CA (US); Carrie Tomasi, Menlo Park, CA (US); Mark Charles Whitcomb, Woodside, CA (US); Eric D. Dowdy, White Rock, NM (US); Wenyi Fu, Edmonton (CA); Patricia MacLeod, Edmonton (CA)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 13/956,905

(22) Filed: Aug. 1, 2013

(65) Prior Publication Data

US 2014/0039194 A1 Feb. 6, 2014

Related U.S. Application Data

(60) Provisional application No. 61/679,475, filed on Aug. 3, 2012.

(51) Int. Cl.
| | | |
|---|---|---|
| *C07C 45/00* | (2006.01) | |
| *C07D 215/00* | (2006.01) | |
| *C07C 49/84* | (2006.01) | |
| *C07C 67/12* | (2006.01) | |
| *C07C 43/225* | (2006.01) | |
| *C07D 215/56* | (2006.01) | |
| *C07C 67/343* | (2006.01) | |
| *C07C 45/46* | (2006.01) | |
| *C07C 45/30* | (2006.01) | |

(52) U.S. Cl.
CPC .............. *C07D 215/56* (2013.01); *C07C 49/84* (2013.01); *C07C 67/12* (2013.01); *C07C 43/225* (2013.01); *C07C 67/343* (2013.01); *C07C 45/46* (2013.01); *C07C 45/30* (2013.01)
USPC .......................................... 546/156; 568/316

(58) Field of Classification Search
CPC .............................. C07D 215/56; C07C 45/63
USPC .......................................... 546/156; 568/316
See application file for complete search history.

(56) References Cited

U.S. PATENT DOCUMENTS

| | | |
|---|---|---|
| 7,176,220 B2 | 2/2007 | Satoh et al. |
| 7,825,252 B2 | 11/2010 | Dowdy et al. |
| 8,153,801 B2 | 4/2012 | Dowdy et al. |
| 8,324,244 B2 | 12/2012 | Dowdy et al. |
| 8,383,819 B2 | 2/2013 | Matsuda et al. |
| 8,440,831 B2 | 5/2013 | Dowdy et al. |
| 2005/0104233 A1 | 5/2005 | Satoh et al. |
| 2008/0125594 A1 | 5/2008 | Dowdy et al. |
| 2008/0207618 A1 | 8/2008 | Satoh et al. |
| 2009/0036684 A1 | 2/2009 | Matsuda et al. |
| 2009/0093467 A1 | 4/2009 | Kearney et al. |
| 2009/0093482 A1 | 4/2009 | Kearney et al. |
| 2009/0099366 A1 | 4/2009 | Dowdy et al. |
| 2009/0233964 A1 | 9/2009 | Kearney et al. |
| 2009/0318702 A1 | 12/2009 | Matsuda et al. |
| 2010/0331331 A1 | 12/2010 | Kearney et al. |
| 2011/0009411 A1 | 1/2011 | Kearney et al. |
| 2012/0238758 A1 | 9/2012 | Dowdy et al. |
| 2013/0116437 A1 | 5/2013 | Dowdy et al. |
| 2013/0253200 A1 | 9/2013 | Dowdy et al. |

FOREIGN PATENT DOCUMENTS

| | | |
|---|---|---|
| CA | 2470365 A1 | 6/2004 |
| EA | 200870321 A1 | 2/2009 |
| EP | 1 564 210 A1 | 8/2005 |
| EP | 1 582 523 A1 | 10/2005 |
| EP | 1 582 524 A1 | 10/2005 |
| EP | 1 992 607 A1 | 11/2008 |
| JP | 4669040 B2 | 4/2011 |
| WO | WO-02/48113 A1 | 6/2002 |
| WO | WO-03/043992 A1 | 5/2003 |
| WO | WO-2004/013103 A2 | 2/2004 |
| WO | WO-2004/013103 A3 | 2/2004 |
| WO | WO-2004/031159 A1 | 4/2004 |
| WO | WO-2004/046115 A1 | 6/2004 |
| WO | WO-2005/112930 A1 | 12/2005 |
| WO | WO-2005/113508 A1 | 12/2005 |
| WO | WO-2005/113509 A1 | 12/2005 |
| WO | WO-2007/063869 A1 | 6/2007 |
| WO | WO-2007/102512 A1 | 9/2007 |
| WO | WO-2008/033836 A2 | 3/2008 |
| WO | WO-2008/033836 A3 | 3/2008 |
| WO | WO-2009/036161 A1 | 3/2009 |

OTHER PUBLICATIONS

Abdel-Aziz, A.A-M. et al. (2005). "Lewis acid-promoted transformation of 2-alkoxypyridines into 2-aminopyridines and their antibacterial activity. Part 2: Remarkably facile C—N bond formation," *Bioorg. And Med. Chem.* 13:4929-4935.

Andrianov, K.A. et al. (1977). "On the reactions of trialkyl(aryl)hydrosilanes with trifluoroacetic acid," Journal of Organometallic Chemistry 128:43-55.

Bailey, W.F. et al. (1988). "The Mechanism of the Lithium-Halogen Interchange Reaction: A Review of the Literature," Journal of Organometallic Chemistry 352:1-46.

Barnes D.M. et al. (2002). "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to the Synthesis of the Antidepressant Rolipram," *J. Am. Chem. Soc.* 124:13097.

Beak, P. et al. (1997). "The reaction of n-butyllithium with benzoic acid: is nucleophilic addition competitive with deprotonation?" Journal of Physical Organic Chemistry 10:537-541.

Bowden S.A. et al. (2004). "A New Approach to Rapid Parallel Development of Four Neurokinin Antagonists. Part 4. Synthesis of ZD2249 Methoxy Sulfoxide," *Organic Process Research and Development* 8:33-44.

(Continued)

*Primary Examiner* — John Mabry
(74) *Attorney, Agent, or Firm* — Morrison & Foerster LLP

(57) ABSTRACT

The invention provides synthetic processes and synthetic intermediates that can be used to prepare 4-oxoquinolone compounds having useful integrase inhibiting properties.

21 Claims, No Drawings

(56) References Cited

OTHER PUBLICATIONS

Da Silva, A. D. et al. (2003). "Biological Activity and Synthetic Methodologies for the Preparation of Fluoroquinolines, A Class of Potent Antibacterial Agents," *Current Medicinal Chemistry* 10:21-39.
Kato, S. et al. (2002). "Non-Cryogenic Metalation of Aryl Bromides Bearing Proton Donating Groups: Formation of a Stable Magnesia-Intermediate," *Tetrahedron Lett.* 43:7315-7317.
Kursanov, D.N. et al. (1974). "Applications of Ionic Hydrogenation to Organic Synthesis," *Synthesis* 633-651.
Leysen, D.C. et al. (1991). "Synthesis of Antibacterial 4-Quinoline-3-Carboxylic Acids and their Derivatives Part 1," *Die Pharmazie* 46:485-501.
Leysen, D.C. et al. (1991). "Synthesis of Antibacterial 4-Quinoline-3-Carboxylic Acids and their Derivatives Part 2," *Die Pharmazie* 46:557-572.
Radl, S.V. et al. (1992). "Recent Advances in the Synthesis of Antibacterial Quinolones," *Heterocycles* 34-11:2143-2177.
Sato, M. et al. (Mar. 5, 2006). "Novel HIV-1 Integrase Inhibitors Derived from Quinolone Antibiotics," *J. Medicinal Chem.* 49(5):1506-1508.
Smith et al. (2001). "March's Advanced Organic Chemistry: Reactions, Mechanisms, and Structure," Wiley-Interscience Publication, John Wiley & Son, p. 564, 5th ed.
Sorbera, L.A. et al. (Jan. 1, 2006). "GS-9137: Anti-HIV Agent HIV Integrase Inhibitor," *Drugs of the Future* 31(4):310-313.
Non-Final Office Action mailed on Apr. 27, 2011, for U.S. Patent No. 8,153,801, issued on Apr. 10, 2012, ten pages.
Non-Final Office Action mailed on Oct. 1, 2013, for U.S. Appl. No. 13/619,297, filed Sep. 14, 2012, six pages.
Restriction Requirement mailed on Jun. 28, 2011, for U.S. Appl. No. 12/208,952, filed Sep. 11, 2008, six pages.
Notice of Allowance mailed on Feb. 12, 2014 for U.S. Appl. No. 13/868,836, filed Apr. 23, 2013, nine pages.
Notice of Allowance mailed on Mar. 27, 2014, for U.S. Appl. No. 13/619,297, filed Sep. 14, 2012, eight pages.
African Regional Office Action mailed on Sep. 26, 2013, for African Regional Patent Application No. AP/P/2009/004831, filed on Sep. 11, 2007, five pages.
Canadian Office Action mailed on Mar. 31, 2014, for Canadian Patent Application No. 2,661,943, filed on Sep. 11, 2007, two pages.
Canadian Office Action mailed on Feb. 7, 2014 for Canadian Patent Application No. 2,698,245, filed on Sep. 11, 2008, two pages.
Chinese Office Action mailed on Nov. 11, 2013 for Chinese Patent Application No. 2008801065542, filed on Sep. 11, 2008, eleven pages.
Eurasian Office Action mailed on Dec. 19, 2013, for Eurasian Patent Application No. 2009-00441 filed on Sep. 11, 2007, fifteen pages.
International Search Report mailed on Nov. 18, 2008, for PCT Patent Application No. PCT/US2008/076002 filed on Sep. 11, 2008, two pages.
International Search Report mailed on Mar. 4, 2008, for PCT Patent Application No. PCT/US2007/078157 filed on Sep. 11, 2007, three pages.
International Search Report mailed on Oct. 28, 2013, for PCT Patent Application No. PCT/US2013/053295 filed on Aug. 1, 2013, four pages.
Notice of Allowance mailed on Sep. 24, 2013 for Mexican Patent Application No. MXA/2010/002783, filed on Sep. 11, 2008, one page.
Notice of Allowance mailed on Dec. 18, 2013 for Israeli Patent Application No. 220311, filed on Sep. 11, 2007, four pages.
Israeli Office Action mailed on Oct. 30, 2013 for Israeli Patent Application No. 204206, filed on Sep. 11, 2008, two pages.
Notice of Allowance mailed on Oct. 1, 2013 for Australian Patent Application No. 2008298943, filed on Sep. 11, 2008, two pages.
Written Opinion of the International Searching Authority mailed on Oct. 28, 2013, for PCT Patent Application No. PCT/US2013/053295 filed on Aug. 1, 2013, six pages.
Written Opinion of the International Searching Authority mailed on Nov. 18, 2008, for PCT Patent Application No. PCT/US2008/076002 filed on Sep. 11, 2008, five pages.
Written Opinion of the International Searching Authority mailed on Mar. 4, 2008, for PCT Patent Application No. PCT/US2007/078157 filed on Sep. 11, 2007, six pages.
European Communication mailed on May 18, 2012, for European Patent Application No. 08 830 255.9 filed on Sep. 11, 2008, four pages.
European Communication mailed on Sep. 19, 2013, for European Patent Application No. 07 842 242.5 filed on Sep. 11, 2007 four pages.
Extended European Search Report mailed on Sep. 24, 2013, for European Patent Application No. 13 174 174.6 filed on Sep. 11, 2007 eight pages.

PROCESS AND INTERMEDIATES FOR PREPARING INTEGRASE INHIBITORS

CROSS-REFERENCE TO RELATED APPLICATION

This application claims priority to and the benefit under 35 U.S.C. 119(e) of U.S. Provisional Application No. 61/679,475, filed on Aug. 3, 2012, the disclosure of which is hereby incorporated by reference in its entirety.

BACKGROUND OF THE INVENTION

International Patent Application Publication Number WO 2004/046115 provides certain 4-oxoquinolone compounds that are useful as HIV integrase inhibitors. The compounds are reported to be useful as anti-HIV agents.

International Patent Application Publication Number WO 2005/113508 provides certain specific crystalline forms of one of these 4-oxoquinolone compounds (i.e. 6-(3-chloro-2-fluorobenzyl)-1-[(S)-1-hydroxymethyl-2-methylpropyl]-7-methoxy-4-oxo-1,4-dihydroquinolone-3-carboxylic acid). The specific crystalline forms are reported to have superior physical and chemical stability compared to other physical forms of the compound.

International Patent Application WO2009/036161 and International Patent Application WO2008/033836 describe methods for preparing the 4-oxoquinolone compounds reported in WO 2004/046115 and WO 2005/113508.

There is currently a need for improved methods for preparing the 4-oxoquinolone compounds reported in International Patent Application Publication Number WO 2004/046115 and in International Patent Application Publication Number WO 2005/113508. In particular, there is a need for new synthetic methods that are simpler or less expensive to carry out, or that require fewer synthetic steps, or that provide an increased yield, or that eliminate the use of toxic or costly reagents or wherein the starting materials are easier to use or purify.

SUMMARY OF THE INVENTION

The present invention provides new synthetic processes and synthetic intermediates that are useful for preparing the 4-oxoquinolone compounds reported in International Patent Application Publication Number WO 2004/046115 and in International Patent Application Publication Number WO 2005/113508. The compound of formula 13 is one such quinolone compound. In particular, the new synthetic processes and intermediates of the present invention are useful for preparing intermediates (e.g. the compound of formula 9) used to prepare the compound of formula 13.

Accordingly, in one embodiment the invention provides a compound selected from:

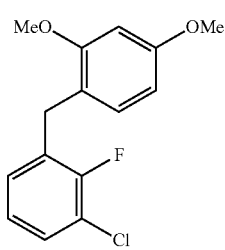

and

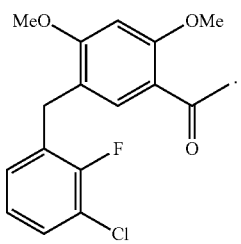

In another embodiment the invention provides the compound:

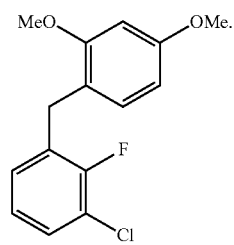

In another embodiment the invention provides the compound:

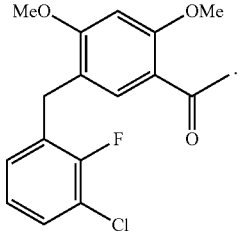

In another embodiment the invention provides a method for preparing a compound of formula 13:

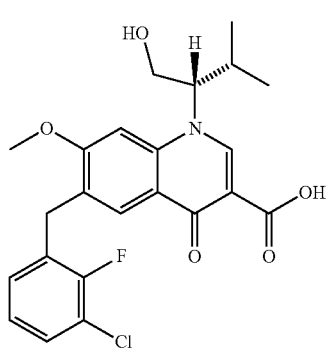

or a salt thereof, comprising converting a compound of formula 8:

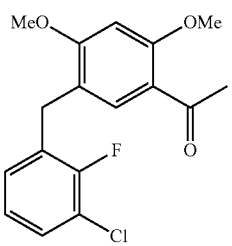

to the compound of formula 13 or the salt thereof.

In another embodiment the invention provides a method for preparing a compound of formula 13:

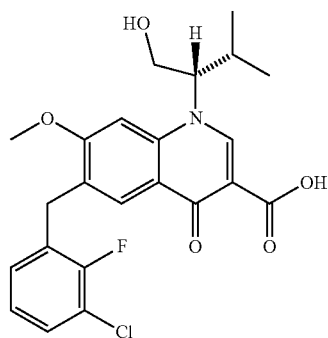

or a salt thereof, comprising converting a compound of formula 4:

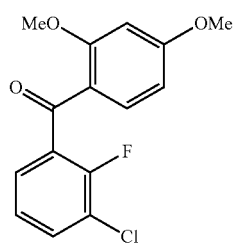

to the compound of formula 13 or the salt thereof.

In another embodiment the invention provides a method for preparing a compound of formula 13:

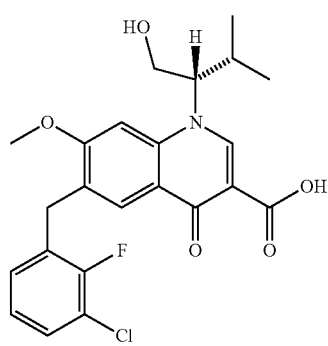

or a salt thereof, comprising converting a compound of formula 5:

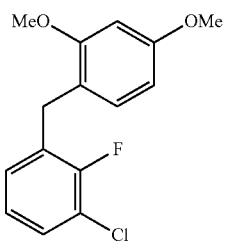

to the compound of formula 13 or the salt thereof.

In another embodiment the invention provides a method for preparing a compound of formula 13:

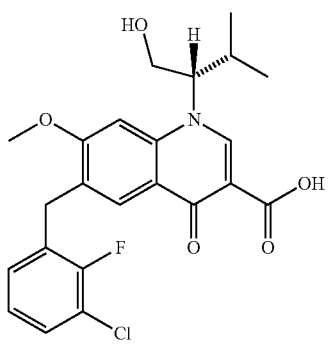

or a salt thereof, comprising converting a compound of formula 2:

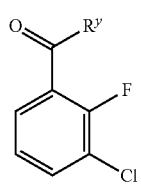

to the compound of formula 13 or the salt thereof, wherein $R^y$ is halogen.

In another embodiment the invention provides a method for preparing a compound of formula 9:

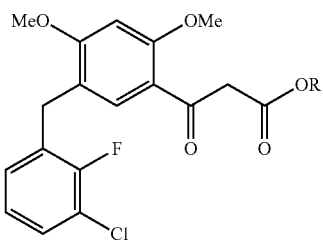

comprising acylating a compound of formula 8:

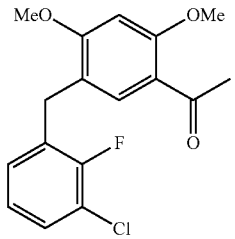
8 to provide the compound of formula 9, wherein R is $(C_1\text{-}C_6)$ alkyl.

In another embodiment the invention provides a method for preparing a compound of formula 8:

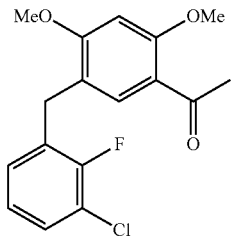
8 comprising acylating a compound of formula 5:

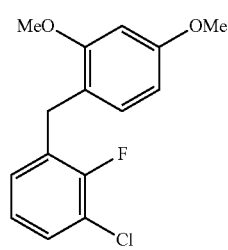
5 to provide the compound of formula 8.

In another embodiment the invention provides a method for preparing a compound of formula 5:

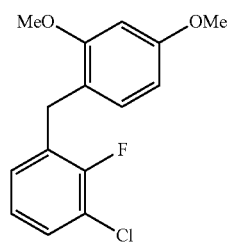
5 comprising reducing a compound of formula 4:

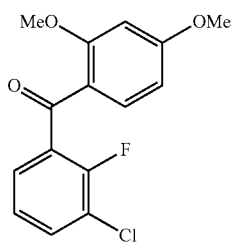
4 to the compound of formula 5.

In another embodiment the invention provides a method for preparing a compound of formula 5:

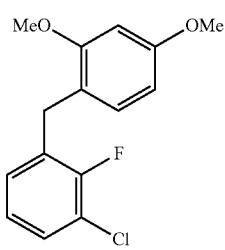
5 comprising arylating a compound of formula 6:

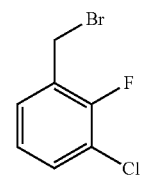
6 to provide the compound of formula 5.

In another embodiment the invention provides a method for preparing a compound of formula 4:

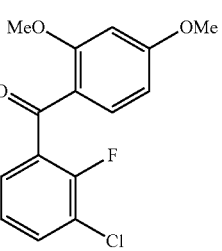
4 comprising converting a compound of formula 2:

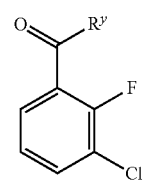
2 to the compound of formula 4, characterized in that the compound of formula 2 is allowed to react with a compound of formula 3:

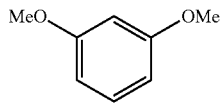
3 to provide the compound of formula 4, wherein $R^y$ is halogen.

In another embodiment the invention provides a method for preparing a compound of formula 4:

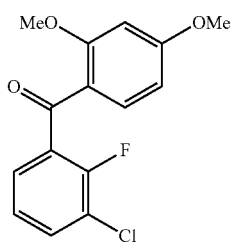
4 comprising arylating a compound of formula 1:

1 to provide the compound of formula 4, characterized in that the compound of formula 1 is arylated with a compound of formula 3:

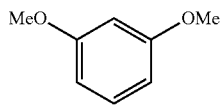
3 to provide the compound of formula 4.

The invention also provides other synthetic processes and synthetic intermediates disclosed herein that are useful for preparing the 4-oxoquinolone compounds.

DETAILED DESCRIPTION

The following definitions are used, unless otherwise described. Halogen, halide or halo is fluoro, chloro, bromo, or iodo. Alkyl denotes both straight and branched groups, but reference to an individual radical such as propyl embraces only the straight chain radical, a branched chain isomer such as isopropyl being specifically referred to.

It will be appreciated by those skilled in the art that a compound having a chiral center may exist in and be isolated in optically active and racemic forms. Some compounds may exhibit polymorphism. It is to be understood that the present invention encompasses processes for preparing any racemic, optically-active, polymorphic, tautomeric, or stereoisomeric form, or mixtures thereof, of a compound described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

It is also to be understood that compounds depicted herein may or may not be shown with absolute stereochemistry. If a compound is drawn with stereochemical bonds (e.g. solid, solid-wedge or dashed or dashed-wedge bonds) it is meant to be the specific stereoisomer shown (e.g diastereomer or enantiomer). Accordingly, wherein applicable, in one embodiment the stereoisomer of a compound depicted herein is about >99% enriched in that stereoisomer. In another embodiment the stereoisomer of a compound depicted herein is about >98% enriched in that stereoisomer. In another embodiment the stereoisomer of a compound depicted herein is about >95% enriched in that stereoisomer. In another embodiment the stereoisomer of a compound depicted herein is about >90% enriched in that stereoisomer. In another embodiment the stereoisomer of a compound depicted herein is about >80% enriched in that stereoisomer. In another embodiment the stereoisomer of a compound depicted herein is about >70% enriched in that stereoisomer. In another embodiment the stereoisomer of a compound depicted herein is about >60% enriched in that stereoisomer. In another embodiment the stereoisomer of a compound depicted herein is about >50% enriched in that stereoisomer.

In cases where compounds identified herein are sufficiently basic or acidic to form stable acid or base salts, the invention also provides salts of such compounds. Such salts may be useful as intermediates, for example, for purifying such compounds. Examples of useful salts include organic acid addition salts formed with acids, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts may be obtained using standard procedures well known in the art, for example by reacting a sufficiently basic compound such as an amine with a suitable acid affording an anion. Alkali metal (for example, sodium, potassium, or lithium) or alkaline earth metal (for example calcium or magnesium) salts of carboxylic acids, for example, can also be made.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl.

A specific value for $R^y$ is Cl.
A specific value for R is ethyl.
A specific value for R is methyl or ethyl.
A specific value for R is methyl.
A specific value for $R_a$ is methyl.
A specific value for $R_b$ is methyl.

Scheme 1 outlines general methods of the invention useful for preparing a compound of formula 9. The methods of preparing the compound of formula 9 as described herein require fewer steps and are more efficient than the methods used to prepare the compound of formula 9 as described in the literature (International Patent Application Publication Number WO 2004/046115 and International Patent Application Publication Number WO 2005/113508) and thus represent a significant improvement over the previous methods. In addition, the starting materials used in the methods to prepare the compound of formula 9 as described herein have advantageous properties including ease of use and ease of purification.

Scheme 1

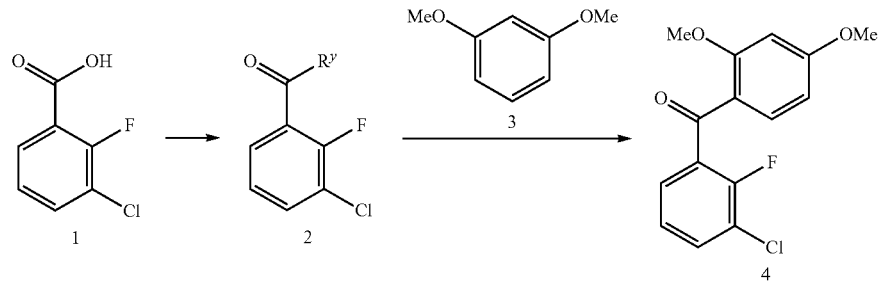

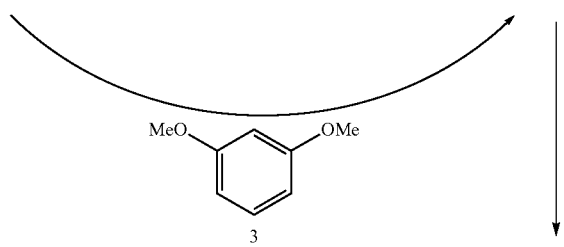

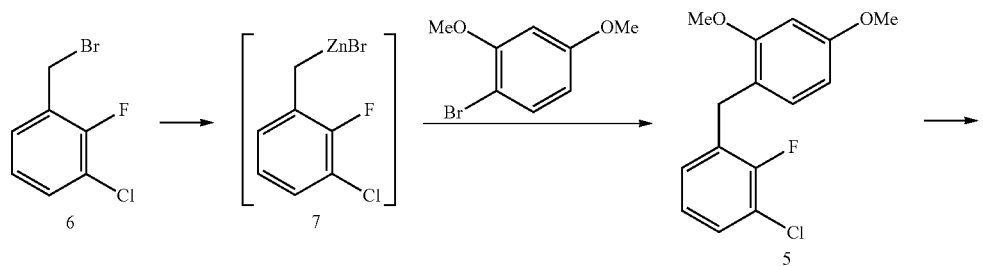

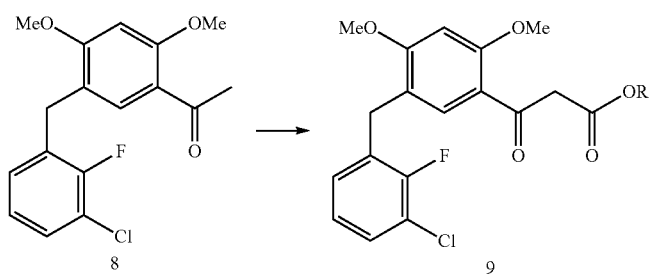

Preparation of a Compound of Formula 4 (Scheme 2).

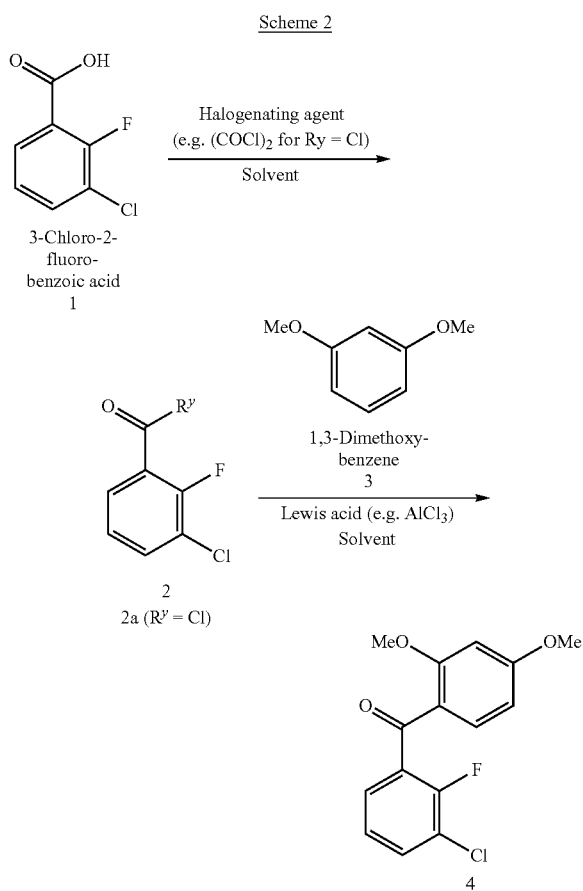

International publication WO 2004/031159 describes the preparation of the compound of formula 4 from 2-fluoro-3-chloro-N-methoxy-N-methylbenzamide and 2,4-dimethoxyphenylmagnesium bromide. The present invention includes an improved method of making compound 4 over the methods of WO 2004/031159 (Scheme 2). The advantages of the current methods include fewer steps to convert compound 1 to compound 4 and the use of compound 1, compound 2 (e.g. compound 2a) and compound 3 directly versus more complex derivatives of these compounds. For instance, the method discussed in WO 2004/031159 requires the organometallic intermediate of compound 3 (i.e. 2,4-dimethoxyphenylmagnesium bromide). Such organometallic derivatives may have certain undesirable properties. In contrast, the present invention utilizes compound 3 directly which also eliminates the extra step of preparing the organometallic reagent. In addition, the literature method requires the use of an amide derivative of compound 1 or compound 2 (i.e. 2-fluoro-3-chloro-N-methoxy-N-methylbenzamide) to prepare compound 4; in contrast the present method utilizes compound 1 and compound 2 (e.g. compound 2a) directly.

In one embodiment the invention provides a method of converting a compound of formula 1 to a compound of formula 4. In another embodiment the invention provides a method of converting a compound of formula 2 to a compound of formula 4, wherein $R^y$ is halo. A specific value for $R^y$ is chloro (i.e. compound 2a). In another embodiment the invention provides a method for converting a compound of formula 1 to a compound of formula 4 wherein a) the compound of formula 1 is converted to a compound of formula 2 and b) the compound of formula 2 is converted to the compound of formula 4.

The compound of formula 1 can be converted to the compound of formula 2, including the compound of formula 2a, by a variety of suitable halogenating agents available to convert a carboxy group to an acid halide group. For example, the compound of formula 1 can be converted to the compound of formula 2a by a variety of suitable reagents available to convert a carboxy group to an acid chloride group including but not limited to oxalyl chloride/N,N-dimethylformamide, thionyl chloride/N,N-dimethylformamide, dimethylmonochlorosilane and phosphorus pentachloride. Suitable solvents include aprotic organic solvents such as halogenated organic solvents (e.g. dichloromethane, chlorobenzene, 1,2-dichloroethane, chloroform or mixtures thereof) and aromatic solvents (e.g. toluene). The reaction can conveniently be carried out at a temperature from about 10° C. to 30° C. The compound of formula 2 (e.g. the compound of formula 2a) can be converted to a compound of formula 4 without isolation of the compound of formula 2 (e.g. the compound of formula 2 can be utilized directly). Thus, the compound of formula 2, as a solution or mixture comprising the solvent and reagents from which it was prepared (as described above), can be converted to the compound of formula 4 as described in the paragraph below. The compound of formula 2 can also be optionally isolated and optionally purified and subsequently converted to a compound of formula 4 as described in the paragraph below.

The compound of formula 2 (e.g. the compound of formula 2a) as described in the paragraph above can be converted to a compound of formula 4 by adding the compound of formula 2 (e.g. as a solution or mixture with the solvent from which it was prepared) to a mixture (e.g. slurry) or solution of the compound of formula 3 and a Lewis acid in a solvent.

The mixture (e.g. slurry) or solution of the compound of formula 3 and a Lewis acid can be prepared by first preparing a mixture of the Lewis acid in an organic solvent. Suitable Lewis acids include but are not limited to aluminum chloride, anhydrous iron chloride, indium(III) chloride, tin(IV) chloride, bismuth chloride, cobalt(III) acetylacetonate, ytterbium triflate, iron(III) sulphate, molybdenum(VI) dichloride dioxide, Amberlyst-15, bismuth(III) triflate, zinc triflate, tin(II) chloride, zinc chloride, scandium triflate, zinc oxide, tin(II) triflate, triflate, gallium(Ill) triflate and hafnium triflate. Suitable solvents include organic solvents such as an aromatic solvent (e.g. toluene) and halogenated organic solvents (e.g. dichloromethane, chlorobenzene, 1,2-dichloroethane, chloroform or mixtures thereof). The addition of the Lewis acid to the solvent can be conveniently carried out at a variety of temperatures such as about 0 to 30° C. to provide the mixture (e.g. slurry) or solution. The mixture (e.g. slurry) or solution of the Lewis acid in the solvent can then be optionally cooled to about 0 to 5° C. at which time the compound of formula 3 is added. In certain embodiments of the invention the temperature is maintained at or below about 28° C. during the addition of the compound of formula 3 to the Lewis acid-solvent. In certain embodiments of the invention the temperature is adjusted to 0 to 5° C. before addition of the compound of formula 2.

The compound of formula 2 (either as a solution as described above or as an isolated compound) can be then be added to the mixture (e.g. slurry) or solution of the compound of formula 3 and the Lewis acid in a solvent. In certain embodiments of the invention the temperature of the reaction of the compound of formula 2 with the compound of formula 3 is maintained at or below about 28° C.

Scheme 3

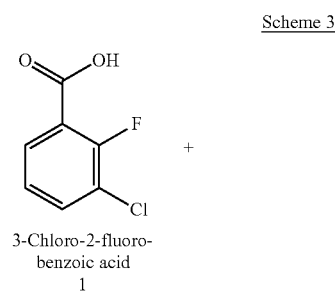

3-Chloro-2-fluoro-
benzoic acid
1

+

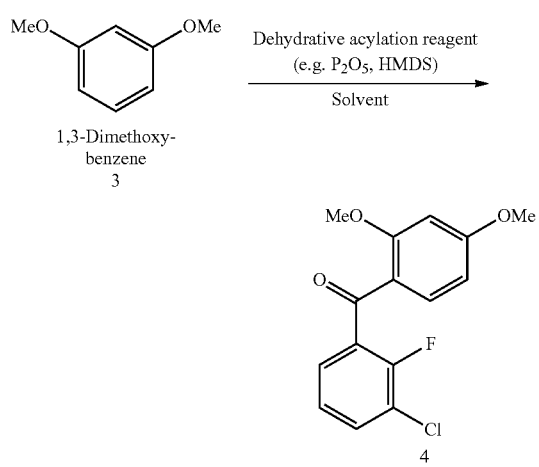

Scheme 4

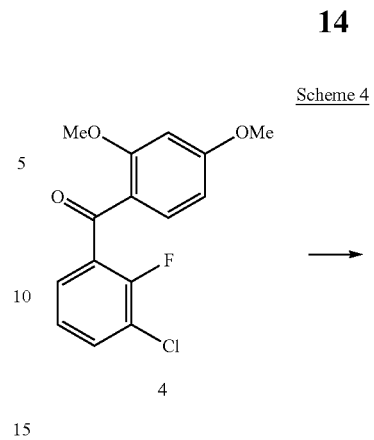

In one embodiment the invention provides a method of reducing a compound of formula 4 to a compound of formula 5 (Scheme 4). The compound of formula 4 can be reduced to provide the compound of formula 5 with a variety of different reducing agents. Suitable reducing agents include but are not limited to aluminum chloride/borane tert-butylamine complex, aluminum chloride/lithium aluminum hydride, trifluoroacetic acid/tetramethyldisiloxane, methanesulfonic acid/tetramethyldisiloxane, trifluoroacetic acid/iodine, phosphoric acid/iodine, acetic acid/iodine, acetic acid-trifluoroacetic acid/iodine, tetramethyldisiloxane/aluminum chloride, triethylsilane/trifluoroacetic acid, tetramethyldisiloxane/trifluoroacetic acid/phosphorus pentoxide, tetramethyldisiloxane/titanium chloride and zinc iodide/sodium cyanoborohydride. Another suitable reducing agent is boron trifluoride (e.g. boron trifluoride etherate)/sodium borohydride. Also included in the invention are any suitable boron agents such as but not limited to boron trifluoride diethyl etherate, boron trifluoride dibutyl etherate, boron trifluoride methyl sulfide, boron trifluoride dehydrate, boron trifluoride tert-butyl methyl ether, boron trifluoride acetic acid, boron trifluoride acetonitrile, boron trifluoride phosphoric acid, boron trifluoride isophorondiamine, boron trifluoride dimethyl ether, boron trifluoride dietherate on alumina and boron trifluoride ethylamine. Suitable solvents include organic solvents such as polar protic and aprotic solvents, halogenated solvents and aromatic solvents (e.g. toluene, 2-methyltetrahydrofuran, 1,2-dichloroethane, tetrahydrofuran, ethanol, chlorobenzene, dichloromethane, ethanol and nitromethane). It is to be readily understood that certain solvents are preferable for certain reducing agents. The reaction can be conveniently carried out at a temperature of about −20° C. to about 30° C. The compound of formula 5 can be conveniently used in isolated form or as a solution in an appropriate solvent (e.g. the solvent from which the compound of formula 5 was prepared) for the conversion of 5 to 8 as described below in Scheme 6.

The compound of formula 1 can also be converted to a compound of formula 4 by combining with a compound of formula 3 and using a suitable dehydrative acylation reagent (Scheme 3). Suitable dehydrative acylation reagents include for example phosphorus pentoxide/HMDS, phosphorus pentoxide/silicon dioxide methanesulfonic acid/phosphorus pentoxide, trifluoromethanesulfonic anhydride, polyphosphoric acid, trifluoroacetic anhydride, trifluoroacetic anhydride/bismuth(III) triflate or scandium triflate, trifluoroacetic anhydride/boron trifluoride diethyl etherate or tetrahydrofurate, trifluoromethanesulfonic anhydride/boron trifluoride diethyl etherate or tetrahydrofurate, trifluoroacetic anhydride/phosphoric acid. Suitable solvents include aprotic organic solvents such as halogenated organic (e.g. 1,2-dichloroethane, dichloromethane) and nitromethane. The reaction can be conveniently carried out at a temperature of about 0-50° C.

In another embodiment the invention further provides a method for the conversion of a compound of formula 4 to a compound of formula 13 or a salt thereof comprising:

a) converting the compound of formula 4, to a compound of formula 9, for example, by the steps outlined in Schemes 4, 6 and 7 and described herein below; and b) converting the compound of formula 9 to the compound of formula 13 or the salt thereof, for example, by any of the steps outlined in Schemes 8-12 and described herein below.

Preparation of a Compound of Formula 5 (Scheme 4).

Scheme 5

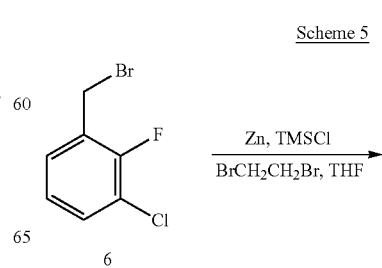

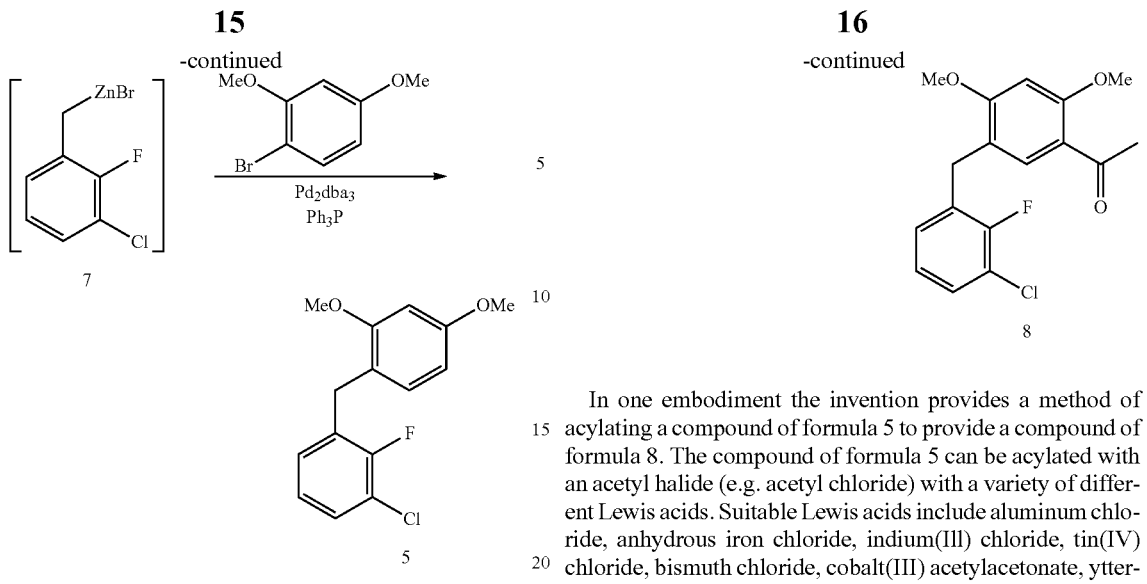

The compound of formula 5 can also be prepared by converting the compound of formula 6 to the compound of formula 5 (Scheme 5). Accordingly, in one embodiment the invention provides a method of converting a compound of formula 6 to a compound of formula 5. The compound of formula 6 can be converted to the compound of formula 5 by first converting the compound of formula 6 to an activated compound (e.g. a zinc compound) such as compound 7 which is then converted to the compound of formula 5. Suitable reagents for the preparation of compound 7 include zinc reagents such as, but not limited to, Zn/TMSCl/1,2-dibromoethane. Suitable reagents for the conversion of compound 7 to compound 5 include catalysts such as, but not limited to, palladium catalysts (e.g. $Pd_2dba_3$) and ligands such as, but not limited to, phosphine-based ligands (e.g. triphenylphosphine). Suitable solvents include organic solvents such as, but not limited to, polar aprotic solvents (e.g. tetrahydrofuran). The reaction can be conveniently carried out at a temperature of about 0° C. to about 65° C.

In another embodiment the invention further provides a method for the conversion of a compound of formula 5 to a compound of formula 13 or a salt thereof comprising:

a) converting the compound of formula 5, to a compound of formula 9, for example, by the steps outlined in Schemes 6 and 7 and described herein below; and b) converting the compound of formula 9 to the compound of formula 13 or the salt thereof, for example, by any of the steps outlined in Schemes 8-12 and described herein below.

Preparation of a Compound of Formula 8 (Scheme 6).

In one embodiment the invention provides a method of acylating a compound of formula 5 to provide a compound of formula 8. The compound of formula 5 can be acylated with an acetyl halide (e.g. acetyl chloride) with a variety of different Lewis acids. Suitable Lewis acids include aluminum chloride, anhydrous iron chloride, indium(III) chloride, tin(IV) chloride, bismuth chloride, cobalt(III) acetylacetonate, ytterbium triflate, iron(III) sulphate, molybdenum(VI) dichloride dioxide, Amberlyst-15, bismuth(III) triflate, zinc triflate, tin (II) chloride, zinc chloride, scandium triflate, zinc oxide, tin(II) triflate, triflate, gallium(III) triflate, hafnium triflate. Suitable solvents include organic solvents such aprotic organic solvents, halogenated solvents and aromatic solvents (e.g. toluene, 2-methyltetrahydrofuran, 1,2-dichloroethane, tetrahydrofuran, chlorobenzene, dichloromethane, and nitromethane). The reaction can be conveniently carried out at a temperature of about −20° C. to about 30° C.

In another embodiment the invention further provides a method for the conversion of a compound of formula 8 to a compound of formula 13 or a salt thereof comprising:

a) converting the compound of formula 8, to a compound of formula 9, for example, by the step outlined in Scheme 7 and described herein below; and b) converting the compound of formula 9 to the compound of formula 13 or the salt thereof, for example, by any of the steps outlined in Schemes 8-12 and described herein below.

Preparation of a Compound of Formula 9 (Scheme 7).

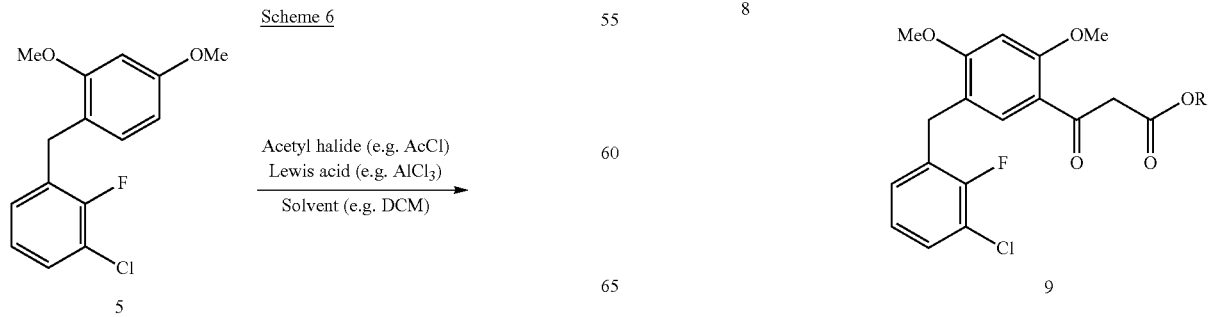

In one embodiment the invention provides a method of acylating a compound of formula 8 to provide a compound of formula 9 wherein R is a $(C_1-C_6)$alkyl (Scheme 7). A specific value for R is ethyl. Another specific value for R is methyl. The compound of formula 8 can be acylated with a variety of different acylating reagents and bases Suitable acylating reagents include dialkyl carbonates such as $((C_1-C_6)alkylO)_2$ $(C=O)$ (e.g. diethyl carbonate). Suitable bases include organic and inorganic bases (e.g. sodium hydride, potassium hydroxide, sodium ethoxide, sodium methoxide, sodium t-amylate, potassium t-amylate, sodium bis(trimethylsilyl) amide). Suitable solvents include organic solvents such aprotic and protic organic solvents and aromatic solvents (e.g. tert-butyl methyl ether, 2-methyltetrahydrofuran, toluene/tetrahydrofuran, tert-butyl methyl ether/tetrahydrofuran, n-butanol, dimethyl sulfoxide). The reaction can be conveniently carried out at a temperature of about 10° C. to about 50° C.

In another embodiment the invention further provides a method for the conversion of a compound of formula 9 (from the compound of formula 8) to a compound of formula 13 or a salt thereof, for example, by any of the steps outlined in Schemes 8-12 and described herein below.

Preparation of a Compound of Formula 13 (Scheme 8).

The compound of formula 9 can be converted to the compound of formula 13, wherein $R_a$ and $R_b$ are each independently $(C_1-C_6)$alkyl and R is $(C_1-C_6)$alkyl, following procedures described in International Patent Application WO2009/036161 (pages 8-26) and in International Patent Application WO2008/033836 (pages 9-34). The entire contents of International Patent Application WO2009/036161 (in particular pages 8-26) and International Patent Application WO2008/033836 (in particular pages 9-34) are incorporated herein by reference. Scheme 8 outlines these procedures in general and Schemes 9-12 describe individual steps.

Scheme 8

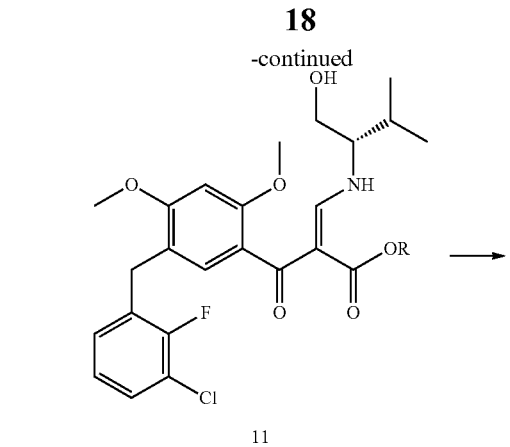

11

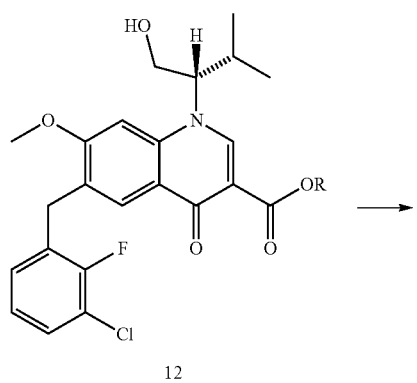

12

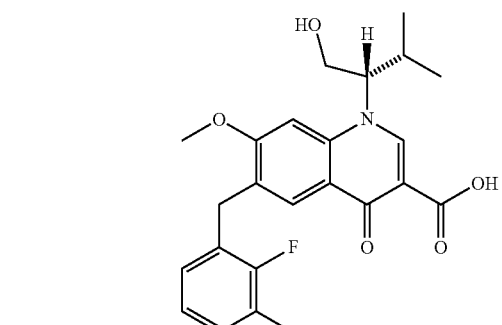

13

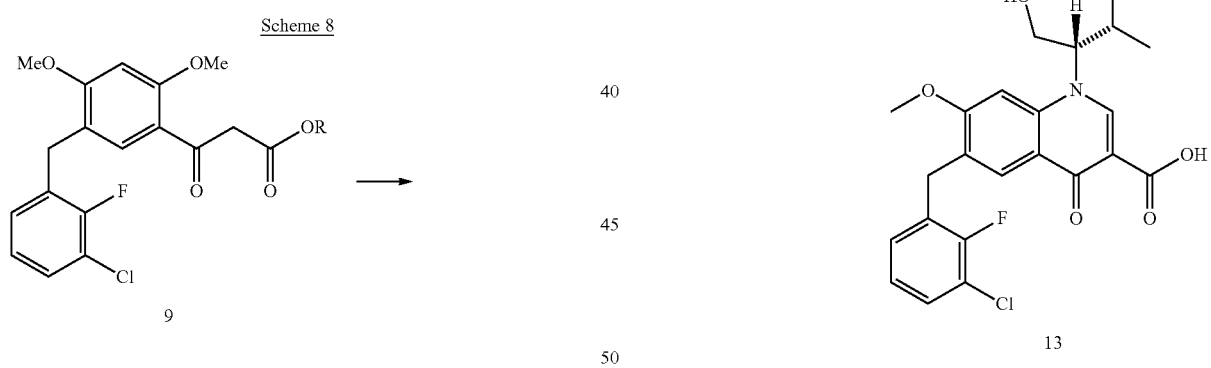

Preparation of a Compound of Formula 10 (Scheme 9).

Scheme 9

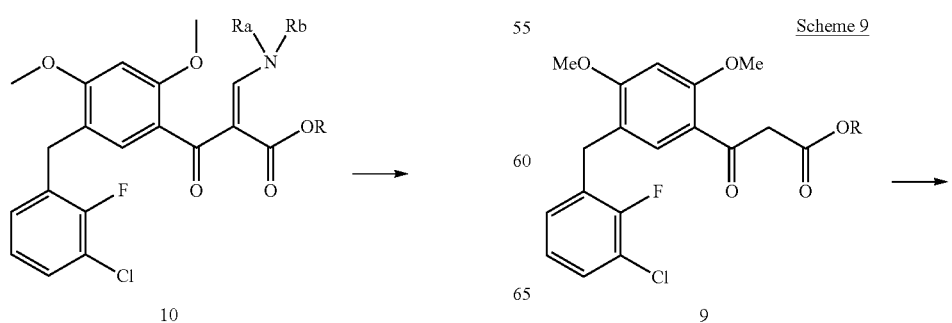

-continued

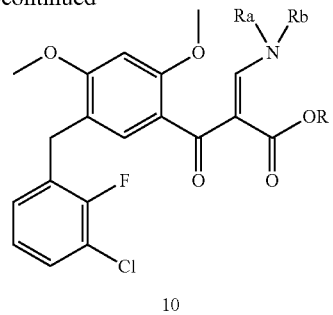

10

The compound of formula 9 or a salt thereof, can be converted to a corresponding compound of formula 10, wherein $R_a$ and $R_b$ are each independently $(C_1-C_6)$alkyl and R is $(C_1-C_6)$alkyl. One specific value for $R_a$ is methyl. One specific value for $R_b$ is methyl. A specific value for R is ethyl. Another specific value for R is methyl. The compound of formula 9 can be converted to an activated alkylidene analog, such as the compound of formula 10, by treatment with a formate group donor such as a dimethylformamide dialkyl acetal (e.g., dimethylformamide dimethyl acetal). The reaction can be carried out at about room temperature or at an elevated temperature (e.g., about 100±50° C.). This reaction may be accelerated by the addition of an acid catalyst, such as, for example, an alkanoic acid, a benzoic acid, a sulfonic acid or a mineral acid. About 500 ppm to 1% acetic acid can conveniently be used. The progress of the reaction can be monitored by any suitable technique (e.g., by HPLC). The compound of formula 10 can be isolated or it can be used directly to prepare the compound of formula 11 as described below.

Preparation of a Compound of Formula 11 (Scheme 10).

Scheme 10

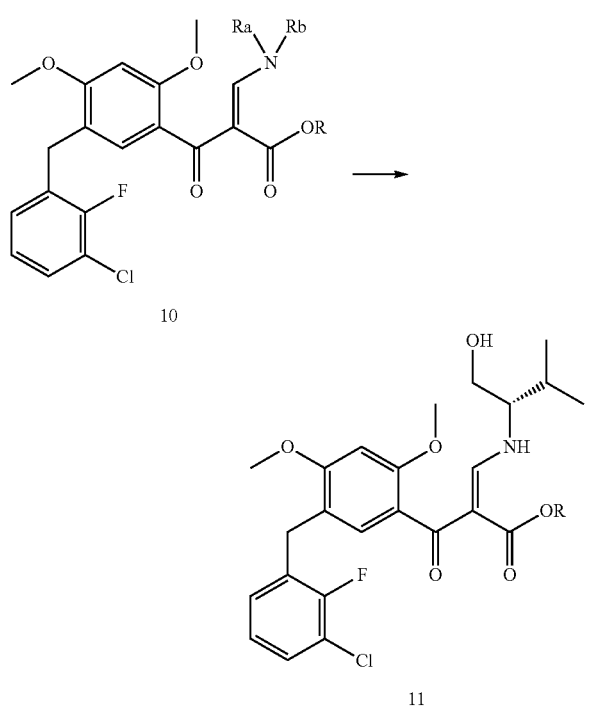

Compound 10 can be combined with (S)-2-amino-3-methyl-1-butanol (S-Valinol, about 1.1 equivalents) to provide compound 11. The progress of the reaction can be monitored by any suitable technique (e.g., by HPLC). The compound of formula 11 can be isolated or used directly to prepare a compound of formula 12 as described below.

Preparation of a Compound of Formula 12 (Scheme 11).

Scheme 11

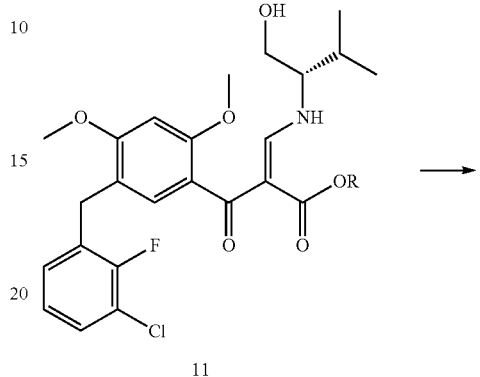

11

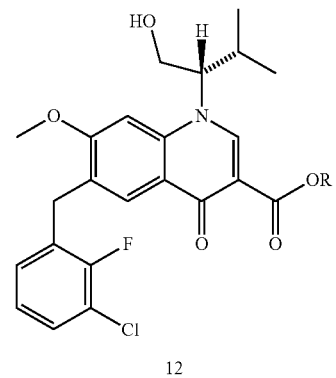 [SMILES: COc1cc2c(cc1Cc1cccc(Cl)c1F)c(=O)c(C(=O)O)cn2[C@H](CO)C(C)C]

12

The compound of formula 11 can be cyclized to provide a compound of formula 12 by treatment with a silylating reagent (e.g. N,O-bis(trimethylsilyl)acetamide, N,O-bis(trimethylsilyl)trifluoroacetamide or hexamethyldisilazane). The reaction can be conducted in a polar aprotic solvent (e.g., dimethylformamide, dimethylacetamide, N-methylpyrrolidinone or acetonitrile). A salt (e.g., potassium chloride, lithium chloride, sodium chloride or magnesium chloride) may be optionally added to accelerate the reaction. The reaction may be conducted at elevated temperature (e.g., a temperature of about 100±20° C.) if necessary to obtain a convenient reaction time. The progress of the reaction can be monitored by any suitable technique (e.g., by HPLC). During the workup, an acid can be used to hydrolyze any silyl ethers that form due to reaction of the silylating reagent with the alcohol moiety of compound 11. Typical acids include mineral acids, sulfonic acids, or alkanoic acids. One specific acid that can be used is aqueous hydrochloric acid. Upon completion of the hydrolysis, Compound 12 can be isolated by any suitable method (e.g., by chromatography or by crystallization). In the above conversion, the silating reagent transiently protects the alcohol and is subsequently removed. This eliminates the need for separate protection and deprotection steps, thereby increasing the efficiency of the conversion.

Preparation of a Compound of Formula 13 (Scheme 12).

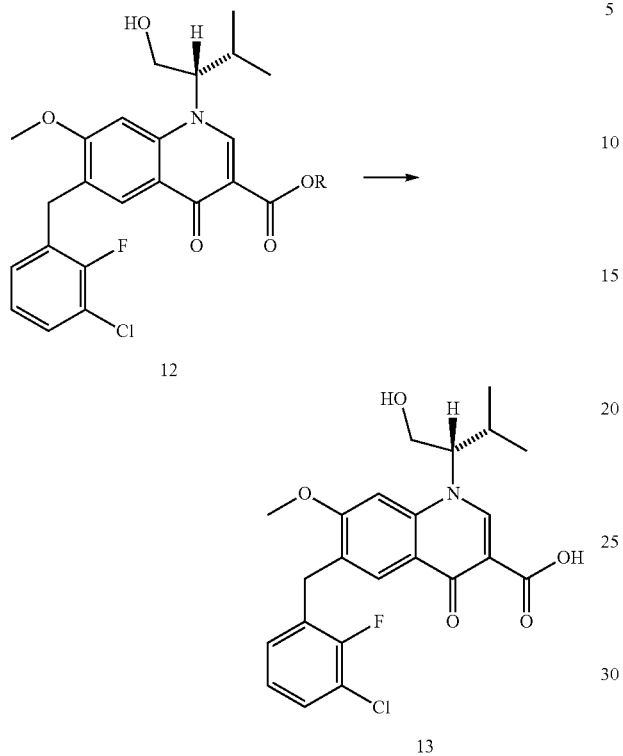

The compound of formula 12 can be converted to a compound of formula 13 by treatment with a suitable base (e.g., potassium hydroxide, sodium hydroxide or lithium hydroxide). For example, about 1.3 equivalents of potassium hydroxide can conveniently be used. This reaction may be conducted in any suitable solvent, such as, for example, tetrahydrofuran, methanol, ethanol or isopropanol, or a mixture thereof. The solvent can also include water. A mixture of isopropanol and water can conveniently be used. The progress of the reaction can be monitored by any suitable technique (e.g., by HPLC). The initially formed carboxylate salt can be neutralized by treatment with an acid (e.g., hydrochloric acid or acetic acid). For example, about 1.5 equivalents of acetic acid can conveniently be used. Following neutralization, the compound of formula 13 can be isolated using any suitable technique (e.g., by chromatography or crystallization).

The compound of formula 13 can be crystallized by adding a seed crystal to a solution that comprises the compound of formula 13. International Patent Application Publication Number WO 2005/113508 provides certain specific crystalline forms of 6-(3-chloro-2-fluorobenzyl)-1-[(S)-1-hydroxymethyl-2-methylpropyl]-7-methoxy-4-oxo-1,4-dihydroquinolone-3-carboxylic acid. The entire contents of International Patent Application Publication Number WO 2005/113508 are incorporated herein by reference (in particular, see pages 12-62 therein). The specific crystalline forms are identified therein as Crystal Form II and Crystal Form III. Crystal form II has an X-ray powder diffraction pattern having characteristic diffraction peaks at diffraction angles 2θ(°) of 6.56, 13.20, 19.86, 20.84, 21.22, and 25.22 as measured by an X-ray powder diffractometer. Crystal form III has an X-ray powder diffraction pattern having characteristic diffraction peaks at diffraction angles) 2θ(°) of 8.54, 14.02, 15.68, 17.06, 17.24, 24.16, and 25.74 as measured by an X-ray powder diffractometer. International Patent Application Publication Number WO 2005/113508 also describes how to prepare a crystalline form of 6-(3-chloro-2-fluorobenzyl)-1-[(S)-1-hydroxymethyl-2-methylpropyl]-7-methoxy-4-oxo-1,4-dihydroquinolone-3-carboxylic acid that have an extrapolated onset temperature of about 162.1° C., as well as how to prepare a seed crystal having a purity of crystal of not less than about 70%. Accordingly, seed crystals of 6-(3-chloro-2-fluorobenzyl)-1-[(S)-1-hydroxymethyl-2-methylpropyl]-7-methoxy-4-oxo-1,4-dihydroquinolone-3-carboxylic acid can optionally be prepared as described in International Patent Application Publication Number WO 2005/113508. Advantageously, the process illustrated in Scheme 8 above provides a crude mixture of the compound of formula 13 that can be directly crystallized to provide Crystal Form III without additional purification (e.g. without the prior formation of another polymorph such as Crystal Form II, or without some other form of prior purification).

Enumerated Embodiments

The following enumerated embodiments are representative of some aspects of the invention.

1. A compound selected from:

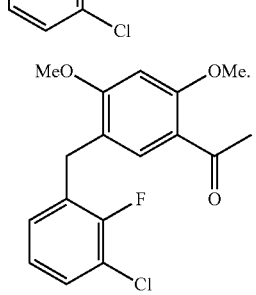

2. The compound of embodiment 1, wherein the compound is:

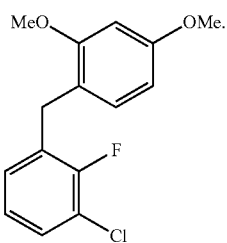

3. The compound of embodiment 1, wherein the compound is:

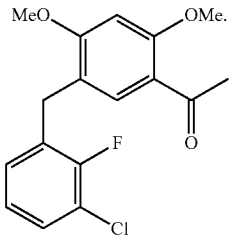

4. A method for preparing a compound of formula 13:

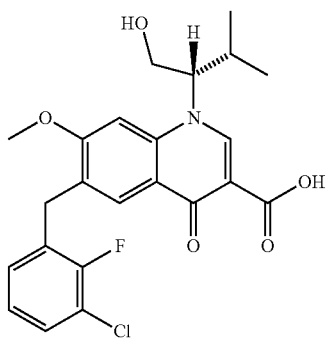

or a salt thereof, comprising converting a compound of formula 8:

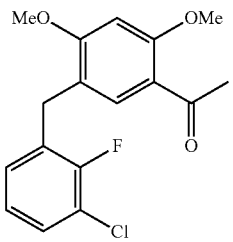

to the compound of formula 13 or the salt thereof.

5. A method for preparing a compound of formula 8:

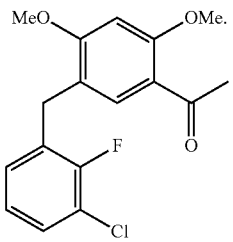

comprising acylating a compound of formula 5:

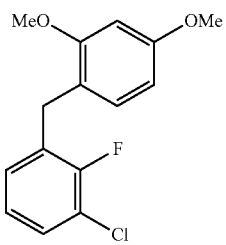

to provide the compound of formula 8.

6. The method of embodiment 5 wherein the compound of formula 5 is acylated with an acetyl halide.

7. The method of embodiment 5 or embodiment 6 wherein the acylation is carried out in the presence of a Lewis acid.

8. The method of embodiment 7 wherein the Lewis acid is aluminum trichloride.

9. A method for preparing a compound of formula 9:

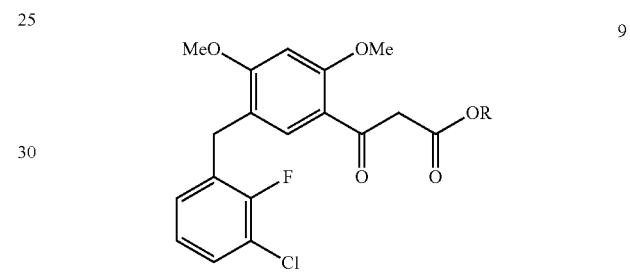

comprising acylating a compound of formula 8:

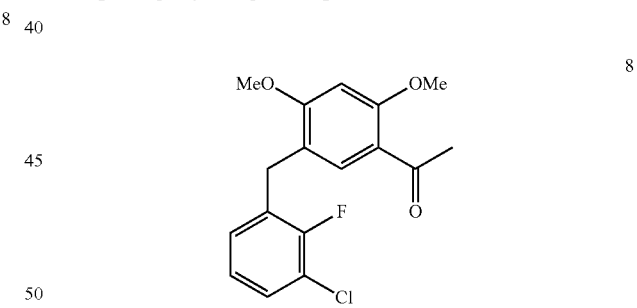

to provide the compound of formula 9, wherein R is $(C_1-C_6)$ alkyl.

10. The method of embodiment 9 wherein R is ethyl.

11. The method of embodiment 9 or embodiment 10 wherein the compound of formula 8 is acylated with diethyl carbonate.

12. The method of any one of embodiments 9-11 wherein the acylation utilizes a base.

13. The method of embodiment 12 wherein the base is a metal alkoxide.

14. The method of any one of embodiments 5-8 further comprising converting the compound of formula 8 to a compound of formula 9:

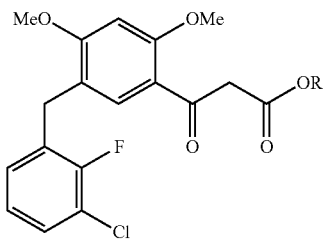

9 wherein R is $(C_1-C_6)$alkyl.

15. The method of embodiment 9 or embodiment 14 further comprising converting the compound of formula 9 to a compound of formula 10:

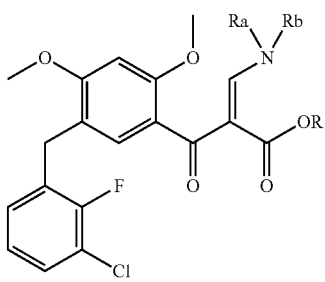

10 or a salt thereof, wherein $R_a$ and $R_b$ are each $(C_1-C_6)$alkyl.

16. The method of embodiment 15 wherein $R_a$ and $R_b$ are each methyl.

17. The method of embodiment 15 or embodiment 16 further comprising converting the compound of formula 10 or the salt thereof, to a compound of formula 11:

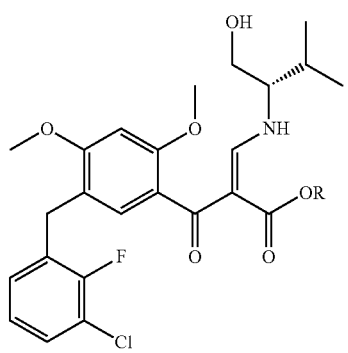

11 or a salt thereof.

18. The method of embodiment 17 further comprising converting the compound of formula 11 or the salt thereof, to a compound of formula 12:

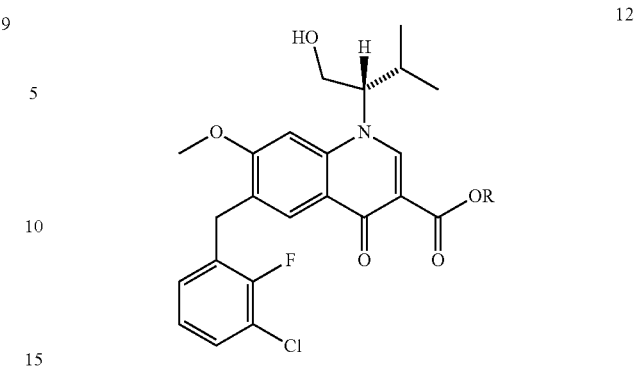

12 or a salt thereof.

19. The method of embodiment 18 further comprising converting the compound of formula 12 or the salt thereof, to a compound of formula 13:

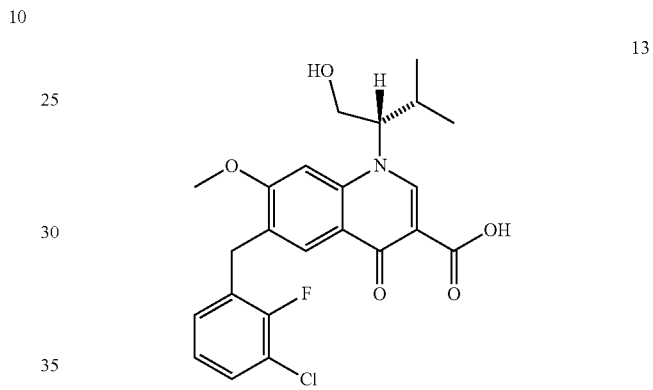

13 or a salt thereof.

20. The method of embodiment 4 further comprising converting the compound of formula 8 to the compound of formula 13 or the salt thereof by any of the methods described in any one of embodiments 9-13 or 15-19.

EXAMPLES

The invention will now be illustrated by the following non-limiting examples.

Example 1

Preparation of (3-chloro-2-fluoro-phenyl)-2,4-dimethoxyphenyl)-methanone (4)

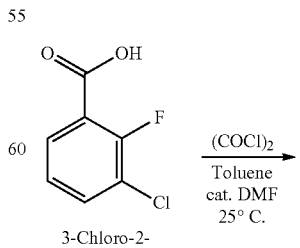

3-Chloro-2-fluoro-benzoic acid
1

-continued

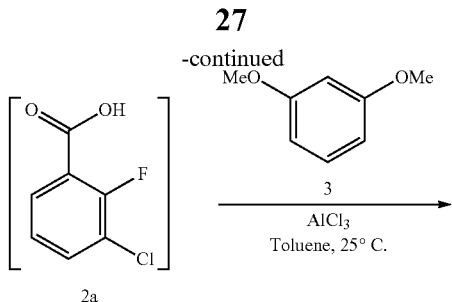

3-Chloro-2-fluorobenzoic acid (1 eq) was combined with toluene (3.23 volumes) and catalytic N,N-dimethylformamide (0.1 eq) and agitated to form a slurry. To the slurry was slowly charged oxalyl chloride (1.1 eq) while maintaining the temperature of the mixture at not more than 28° C. The mixture was agitated at 19 to 25° C. and the conversion to the acid chloride was monitored by HPLC.

In a separate vessel aluminum chloride (1.3 eq) was combined with toluene (1.85 volumes). The mixture was agitated to form a slurry. The slurry was cooled to 0 to 5° C. before slowly adding 1,3-dimethoxybenzene (1.3 eq) while maintaining the temperature at not more than 28° C. After the addition of 1,3-dimethoxybenzene the content of the mixture was adjusted to 0 to 5° C.

When the formation of the acid chloride was complete, it was added to the mixture of aluminum chloride and 1,3-dimethoxybenzene while maintaining the temperature at not more than 28° C. Following completion of the addition, the mixture was allowed to warm to 19 to 25° C. and agitated until complete conversion was observed by HPLC. The reaction was then quenched by slowly transferring the mixture into cold water (5 volumes at 5-10° C.) while maintaining the temperature of the quenched mixture at not more than 28° C. The organic phase was separated and washed with 10% brine solution (4 volumes), and then with an aqueous sodium chloride-ammonium hydroxide mixture (4 volumes of water, 0.5 volumes of sodium chloride and 0.22 volumes of 28% ammonium hydroxide). The organic phase was separated and concentrated by vacuum distillation. The solvent was exchanged to 2-propanol by coevaporation under vacuum. Heptane (4.39 volumes) was charged to the slurry mixture and cooled to 0 to 6° C. The solid was collected by filtration and the wet cake was washed with a mixture of 2-propanol and heptane. The wet solid was dried under vacuum at not more than 40° C. to yield approximately 70% of compound 4 as off-white to light brown solid. $^1$H NMR (CDCl$_3$) δ 7.69 (d, 1H, J=8 Hz), 7.44-7.54 (m, 2H), 7.15 (td, 1H, J=8, 1 Hz), 6.57 (dd, 1H, J=8, 2 Hz), 6.44 (d, 1H, J=2 Hz), 3.88 (s, 3H), 3.66 (s, 3H).

Example 2

Preparation of (3-chloro-2-fluoro-phenyl)-2,4-dimethoxyphenyl) methanone (4)

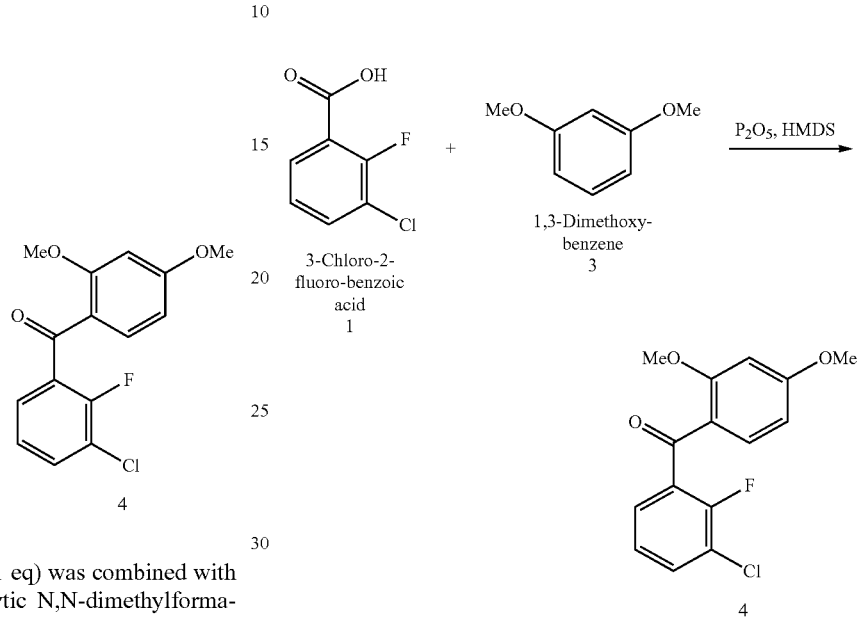

Chlorobenzene (8 volumes) and phosphorus pentoxide (3.3 eq) were mixed to form a slurry mixture at ambient temperature. HMDS (2.7 eq) was added in one portion followed by additional chlorobenzene (2 volumes) for rinse. The resulting mixture was warmed to 80° C. and stirred at the same temperature for 1 h. Next, 3-chloro-2-fluorobenzoic acid (1.0 equiv), 1,3-dimethoxybenzene (1.05 equiv), and chlorobenzene (300 mL) were mixed in a separate flask. The resulting slurry was heated to 110-120° C. giving a clear solution. The PPSE solution prepared above (2.5 equiv relative to CFBA) was added via an addition funnel over 30 min while the batch temperature was kept at the same range. Once all the PPSE was added, the reaction mixture was heated at 120° C. for 16 h. Once the reaction was complete the batch was cooled to room temperature and diluted with iBuOH (4 volumes) and heptane (4 volumes) with stirring. Water (4 volumes) was added with stirring, the batch color was gradually changed from dark purple to dark orange. The layers were separated, the bottom layer was removed. The top organic layer was sequentially washed with 10% Na$_4$EDTA aqueous solution and water. The organic layer was concentrated to about 2 volumes and flushed with iBuOH to remove most of chlorobenzene. The concentrated crude product solution was stirred at room temperature and seeded. Additional iBuOH was added over 30 min and the resulting slurry was stirred at room temperature overnight. Heptane was added to the slurry over 1 h, and the slurry was stirred at room temperature for 2 h, then at 0-5° C. for 1 h. The slurry was filtered and the residual solid in the flask was rinsed with cold mother liquor. The wet cake was washed with cold 10/90 (iBuOH/heptane) followed by cold heptane, and dried under vacuum. Compound 4 was obtained as a beige solid in approximately 60% isolated with ¹H NMR characterization data that matched compound 4 of example 1.

Example 3

Preparation of 1-chloro-3-(2,4-dimethoxybenzyl)-2-fluorobenzene (5)

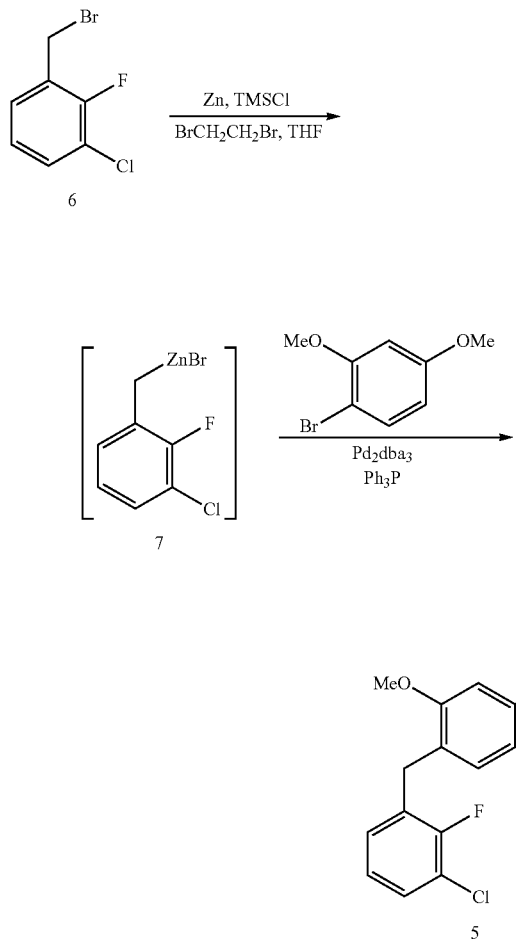

THF (5 volumes) and zinc dust (2.4 eq) were charged to a round bottom flask under nitrogen. The slurry was heated to 60° C. and held for 15 min. 1,2-Dibromoethane (0.2 eq) was added and the mixture agitated at 60° C. for 30 min. The mixture was cooled to ambient temperature before 0.4 eq. chlorotrimethylsilane was added. 3-Chloro-2-fluorobenzyl-bromide (2.0 eq) dissolved in THF was added over 2 h at 0° C. Agitation was stopped and the mixture allowed to settle overnight to give 7 as a solution in THF. Next, 0.16 eq Pd₂dba₃ and 0.35 eq. triphenylphosphine were charged to a separate flask under argon. THF (10 volumes) and 1-bromo-2,4-dimethoxybenzene were added followed by the solution of compound 7 prepared above. The mixture was heated to 65° C. and agitated overnight. The mixture was cooled to room temperature and quenched with aqueous NH₄OH. The organic phase was purified by column chromatography to yield compound 5: ¹H NMR (400 MHz, CDCl₃): δ 7.33 (td, 1H, J=7, 2 Hz), 7.07-6.99 (m, 2H), 6.91 (d, 1H, J=8 Hz), 6.49 (d, 1H, J=8 Hz), 6.40 (dd, 1H, J=8, 2 Hz), 3.80 (s, 2H), 3.68 (s, 3H), 3.67 (s, 3H).

Example 4

Preparation of 1-[5-(3-chloro-2-fluoro-benzyl)-2,4-dimethoxyphenyl]-ethanone (8)

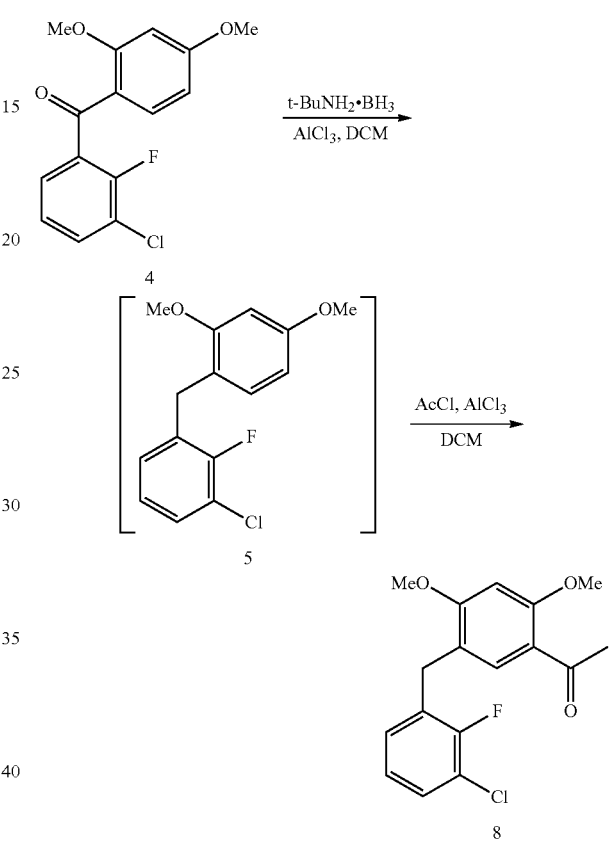

Compound 4 (1 eq) was combined with dichloromethane (1.89 volumes) and agitated to form a solution. In a separate vessel, aluminum chloride (1.02 eq) and dichloromethane (4.91 volumes) were combined to form a slurry. The aluminum chloride mixture was cooled to −13 to −7° C. before the borane tert-butylamine complex (1.12 eq) was added while maintaining the mixture temperature at not more than −7° C. The aluminum chloride mixture was agitated for not less than 1 hour at the same temperature. The compound 4 solution was slowly transferred to the aluminum chloride mixture while maintaining the temperature at −13 to −7° C. The mixture was agitated at the same temperature for approximately 1 hour before warming to 17 to 23° C. The reduction progress was monitored by HPLC. When the reduction was complete the reaction mixture was cooled to 0 to 5° C. and then quenched with cold dilute aqueous HCl. The mixture was agitated to form a biphasic mixture and the phases were separated. The organic phase was washed with dilute aqueous HCl (5 volumes of water and 0.06 volumes of 37% HCl). After separating the phases, the organic phase was concentrated giving compound 5 as a solution in DCM.

The compound 5 DCM solution was transferred into a clean reactor and cooled to −13 to −7° C. Dichloromethane (6 volumes) was charged and followed by aluminum chloride (1.03 eq) while maintaining the temperature at not more than −7° C. Acetyl chloride (1.12 eq) was slowly charged to the mixture while maintaining the temperature at not more than −10° C. The reaction mixture was agitated at −13 to −7° C. and the progress of the acylation reaction was monitored by HPLC. After the acylation was completed the reaction mixture was transferred onto 5 volumes of cold (2 to 8° C.) water while maintaining the temperature at not more than 25° C. The quenched mixture was allowed to warm to 19 to 25° C. and agitated till a biphasic mixture was formed. The organic phase was separated and washed with water (3 volumes). The organic phase was separated and concentrated by vacuum distillation. The solvent was exchanged to 2-propanol by coevaporation under vacuum. The slurry formed was diluted with 2-propanol (1 volume) and then heated to reflux to form a solution. Heptane (2.9 volumes) was slowly charged to the hot solution and cooled to 0 to 5° C. to form a slurry. The product was isolated by filtration. The wet cake was washed with a mixture of 2-propanol and heptane and dried at not more than 40° C. to yield approximately 75% of compound 8 as an off-white to light pink solid. $^1$H NMR (CDCl$_3$) δ 7.66 (s, 1H), 7.18 (td, 1H, J=7 Hz, 2 Hz), 6.88-6.98 (m, 2H), 6.42 (s, 1H), 3.89-3.92 (m, 5H), 3.85 (s, 3H), 2.55 (s, 3H).

Example 5

Preparation of 1-[5-(3-chloro-2-fluoro-benzyl)-2,4-dimethoxyphenyl]-ethanone (8)

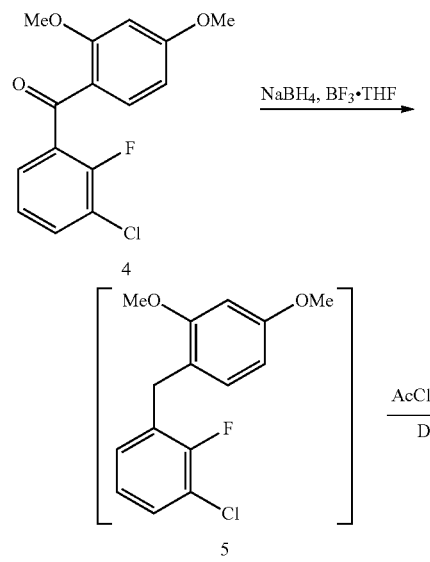

Sodium borohydride (0.81 eq) was combined with tetrahydrofuran (4.5 volumes) to form a slurry. Compound 4 (1 eq) was added to the slurry and the mixture was cooled to about 0° C. Boron trifluoride tetrahydrofuran complex (1.80 eq) was charged slowly while maintaining the temperature at not more than 3° C. After the addition was complete the mixture was allowed to warm to about 28° C. while monitoring the reduction progress by HPLC. After the reduction reaction was complete and the mixture was cooled to about 0° C., the reaction was then quenched by the slow addition of acetone (0.32 volumes, 1.27 eq) while maintaining the temperature of the reaction mixture at not more than 10° C. The mixture was agitated at that temperature briefly followed by slow addition of 5% sodium hydroxide solution (2.89 volumes) while maintaining the temperature of the reaction mixture at not more than 10° C. The mixture was warmed to about 22° C. and agitated for a brief period. The mixture was then concentrated by vacuum distillation before the residue was diluted with ethyl acetate. The biphasic mixture was agitated briefly and the phases were separated. The organic phase was washed with 10% aqueous sodium chloride solution (3 volumes) and concentrated to dryness by vacuum distillation. The residue was co-evaporated with ethyl acetate followed by dichloromethane to provide compound 5 as a dichloromethane stock solution.

The compound 5 DCM solution was transferred into a clean reactor and cooled to −13 to −7° C. Dichloromethane (3 volumes) was charged and then aluminum chloride (1.03 eq) was added to this solution while maintaining the temperature at not more than −7° C. Acetyl chloride (1.12 eq) was slowly charged to the mixture while maintaining the temperature at not more than −10° C. The reaction mixture was agitated at −13 to −7° C. and the progress of the acylation reaction was monitored by HPLC. After the acylation was completed the reaction mixture was transferred into 5 volumes of cold (2 to 8° C.) water while maintaining the temperature at not more than 25° C. The quenched mixture was allowed to warm to 19 to 25° C. and agitated till a biphasic mixture was formed. The organic phase was separated and washed with water (3 volumes). The organic phase was separated and concentrated by vacuum distillation. The solvent was exchanged to 2-propanol by coevaporation under vacuum. The slurry that formed was diluted with 2-propanol (1 volume) and then heated to reflux to form a solution. Heptane (2.92 volumes) was slowly charged to the hot solution and cooled to 0 to 5° C. to form a slurry. The product was isolated by filtration. The wet cake was washed with a mixture of 2-propanol and heptanes and dried at not more than 40° C. to yield approximately 85% of compound 8 as off-white to light pink solid.

Example 6

Preparation of ethyl 3-(5-(3-chloro-2-fluorobenzyl)-2,4-dimethoxyphenyl)-3-oxopropanoate (9')

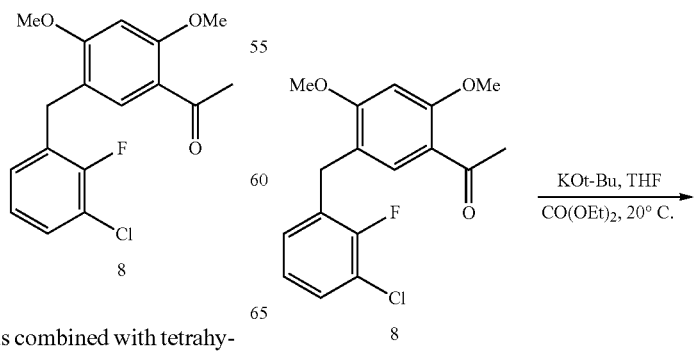

-continued

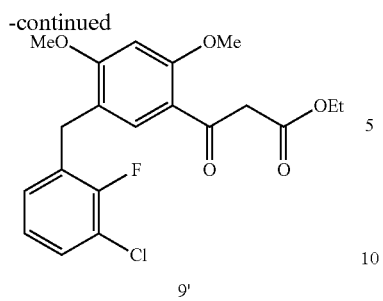
9'

Compound 8 (1 eq) was charged to a well-inerted reactor followed by THF (7.2 volumes) and potassium t-butoxide (2.0 eq). The resulting slurry was degassed thoroughly. In a separate well-inerted reactor, diethyl carbonate (4 eq) was degassed and added slowly to the compound 8 mixture while maintaining the temperature at 19 to 25° C. under an inert atmosphere. The reaction mixture was agitated at 19 to 25° C. until determined to be complete by HPLC. The mixture was cooled to about 8° C. before being quenched with concentrated 37% hydrochloric acid (0.43 volumes) while maintaining the temperature at not more than 22° C. Water was added to the mixture and agitated thoroughly. The phases were separated and the organic phase was washed with 10 wt % aqueous sodium chloride. The phases were separated and the organic phase was concentrated by vacuum distillation. The solvent was exchanged to denatured ethanol by vacuum distillation. Ethanol and water were added and the mixture was warmed to form a solution. The solution was cooled gradually to ambient temperature and then cooled further to 0 to 6° C. The slurry was aged for not less than 3 hours at the same temperature prior to filtration. The wet cake was washed with a mixture of ethanol and water before being dried at not more than 40° C. to yield approximately 85% of compound 9' as a solid. $^1$H NMR (400 MHz, CDCl$_3$): δ 7.76 (s, 1H), 7.21 (td, 1H, J=7, 2 Hz), 6.89-6.98 (m, 2H), 6.40 (s, 1H), 4.18 (q, 2H, J=7 Hz), 3.89-3.93 (m, 8H), 3.87 (s, 2H), 1.24 (t, 3H, J=7 Hz).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound selected from:

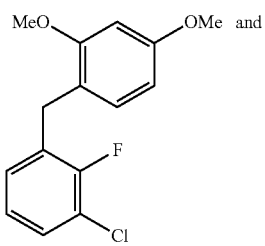

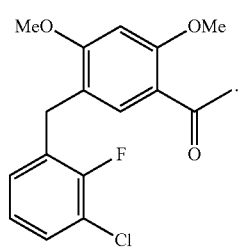

2. The compound of claim 1, wherein the compound is:

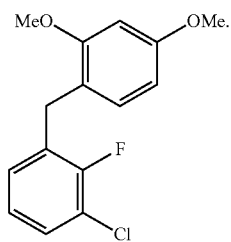

3. The compound of claim 1, wherein the compound is:

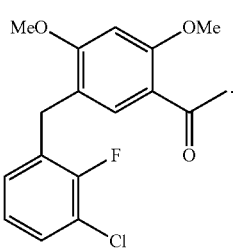

4. A method for preparing a compound of formula 13:

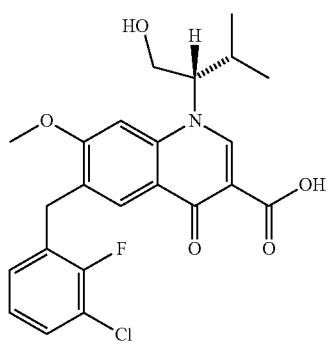

or a salt thereof, comprising converting a compound of formula 8:

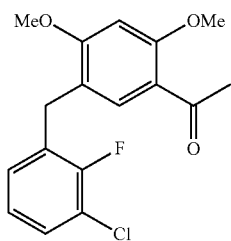

to the compound of formula 13 or the salt thereof.

5. A method for preparing a compound of formula 8:

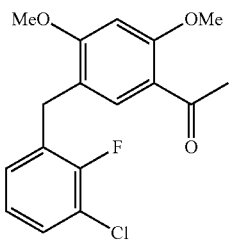

8 comprising acylating a compound of formula 5:

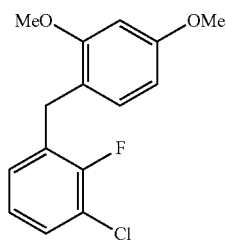

5 to provide the compound of formula 8.

6. The method of claim 5 wherein the compound of formula 5 is acylated with an acetyl halide.

7. The method of claim 5 wherein the acylation is carried out in the presence of a Lewis acid.

8. The method of claim 7 wherein the Lewis acid is aluminum trichloride.

9. A method for preparing a compound of formula 9:

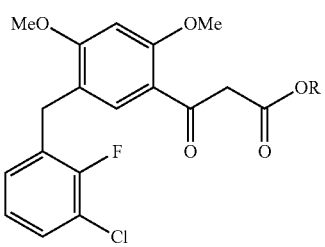

9 comprising acylating a compound of formula 8:

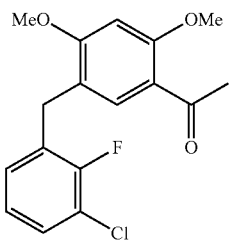

8 to provide the compound of formula 9, wherein R is $(C_1-C_6)$ alkyl.

10. The method of claim 9 wherein R is ethyl.

11. The method of claim 9 wherein the compound of formula 8 is acylated with diethyl carbonate.

12. The method of claim 9 wherein the acylation utilizes a base.

13. The method of claim 12 wherein the base is a metal alkoxide.

14. The method of claim 5 further comprising converting the compound of formula 8 to a compound of formula 9:

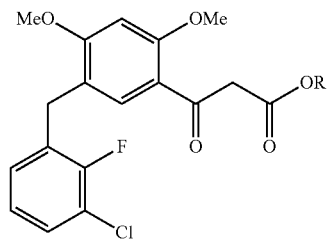

9 wherein R is $(C_1-C_6)$alkyl.

15. The method of claim 9 further comprising converting the compound of formula 9 to a compound of formula 10:

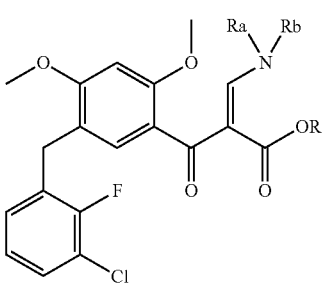

10 or a salt thereof, wherein $R_a$ and $R_b$ are each $(C_1-C_6)$alkyl.

16. The method of claim 15 wherein $R_a$ and $R_b$ are each methyl.

17. The method of claim 15 further comprising converting the compound of formula 10 or the salt thereof, to a compound of formula 11:

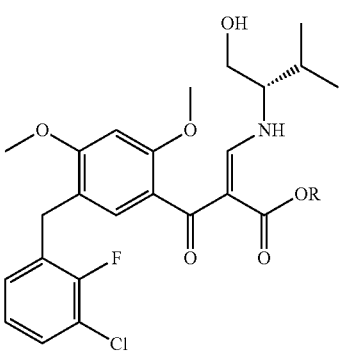

11 or a salt thereof.

18. The method of claim 17 further comprising converting the compound of formula 11 or the salt thereof, to a compound of formula 12:

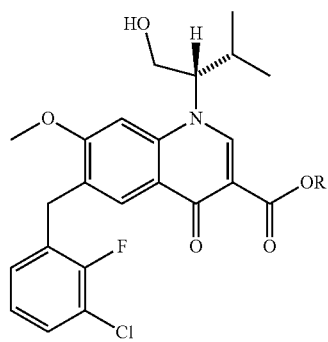

or a salt thereof.

19. The method of claim 18 further comprising converting the compound of formula 12 or the salt thereof, to a compound of formula 13:

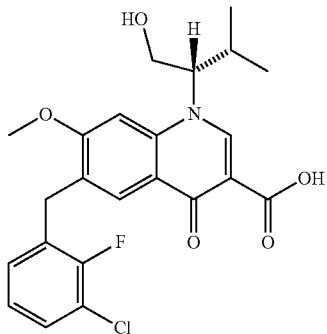

or a salt thereof.

20. The method of claim 4 wherein converting the compound of formula 8 to the compound of formula 13 or the salt thereof comprises the method described in claim 7.

21. The method of claim 4 wherein converting the compound of formula 8 to the compound of formula 13 or the salt thereof comprises the method described in claim 13.

* * * * *